US011324626B2

(12) United States Patent
Aarestad et al.

(10) Patent No.: US 11,324,626 B2
(45) Date of Patent: May 10, 2022

(54) DEVICE AND METHOD FOR OPENING AN AIRWAY

(75) Inventors: Jerome Aarestad, Escondido, CA (US); John Carl Goodman, Missouri City, TX (US)

(73) Assignee: SOMMETRICS, INC., Vista, CA (US)

( * ) Notice: Subject to any disclaimer, the term of this patent is extended or adjusted under 35 U.S.C. 154(b) by 1626 days.

(21) Appl. No.: 13/881,836

(22) PCT Filed: Oct. 26, 2011

(86) PCT No.: PCT/US2011/057906
§ 371 (c)(1),
(2), (4) Date: Jul. 17, 2013

(87) PCT Pub. No.: WO2012/058322
PCT Pub. Date: May 3, 2012

(65) Prior Publication Data
US 2014/0144450 A1    May 29, 2014

Related U.S. Application Data

(60) Provisional application No. 61/406,775, filed on Oct. 26, 2010.

(51) Int. Cl.
*A61F 5/56* (2006.01)
*A61F 5/37* (2006.01)
(Continued)

(52) U.S. Cl.
CPC .............. *A61F 5/3707* (2013.01); *A61F 5/56* (2013.01); *A61H 9/0057* (2013.01); *A61M 1/80* (2021.05); *A61M 16/0488* (2013.01)

(58) Field of Classification Search
CPC .......... A61F 5/56; A61F 5/3707; A61F 5/566; A61H 9/0057; A61M 1/0066; A61M 16/0488
(Continued)

(56) References Cited

U.S. PATENT DOCUMENTS

| 2,931,356 A * | 4/1960 | Schwarz ............... A62B 18/025 |
| | | 128/206.24 |
| 7,182,082 B2 * | 2/2007 | Hoffrichter ............ A61F 5/055 |
| | | 128/200.24 |

(Continued)

FOREIGN PATENT DOCUMENTS

| CN | 101594841 A | 12/2009 |
| JP | H9-503923 A | 4/1997 |

(Continued)

OTHER PUBLICATIONS

International Search Report and Written Opinion dated Mar. 8, 2012 in PCT/US2011/057903.
(Continued)

*Primary Examiner* — Camtu T Nguyen
(74) *Attorney, Agent, or Firm* — Acuity Law Group, P.C.; Michael A. Whittaker

(57) ABSTRACT

A device and a method for creating and/or maintaining an obstruction free upper respiratory passages. The device is configured to fit under the chin of a subject adjacent to the subject's neck at an external location corresponding approximately with the subject's soft tissue associated with the neck's anterior triangle. The device is capable of exerting negative pressure on the surface of a subject's neck, displacing the soft tissue forward and enlarging the airway.

41 Claims, 17 Drawing Sheets

(51) Int. Cl.
*A61M 1/00* (2006.01)
*A61H 9/00* (2006.01)
*A61M 16/04* (2006.01)

(58) Field of Classification Search
USPC .................................. 128/848; 601/148–152
See application file for complete search history.

(56) References Cited

U.S. PATENT DOCUMENTS

| | | | |
|---|---|---|---|
| 7,322,349 B2* | 1/2008 | Power | A61M 15/0085 128/200.14 |
| 7,644,714 B2* | 1/2010 | Atkinson | A61F 5/56 128/848 |
| 7,762,263 B2* | 7/2010 | Aarestad | A61F 5/56 128/848 |
| 2005/0199239 A1* | 9/2005 | Lang | A61M 16/0616 128/206.24 |
| 2006/0009697 A1 | 1/2006 | Banet et al. | |
| 2006/0266369 A1 | 11/2006 | Atkinson et al. | |
| 2007/0144533 A1* | 6/2007 | Nelson | A61F 2/00 128/848 |
| 2008/0110469 A1* | 5/2008 | Weinberg | A41D 13/1176 128/863 |
| 2008/0163875 A1 | 7/2008 | Aarestad et al. | |
| 2010/0229872 A1* | 9/2010 | Ho | A61M 16/0666 128/206.25 |
| 2010/0294284 A1* | 11/2010 | Hohenhorst | A61F 5/012 128/848 |

FOREIGN PATENT DOCUMENTS

| | | | |
|---|---|---|---|
| WO | | 9420041 A1 | 9/1994 |
| WO | | 9634586 A1 | 11/1996 |
| WO | | 00707653 A1 | 2/2000 |
| WO | | 03075739 A2 | 9/2003 |
| WO | | 2008076421 A2 | 6/2008 |
| WO | | 2009112866 A1 | 9/2009 |
| WO | | 2009143259 | 11/2009 |
| WO | | 2009143259 A2 | 11/2009 |
| WO | WO 2009/143259 | * | 11/2009 |
| WO | WO 2009/143259 A2 * | | 11/2009 |
| WO | WO 2009/143259 A3 * | | 11/2009 |
| WO | WO 2017/143259 A2 * | | 11/2009 |
| WO | | 2010068251 A1 | 6/2010 |
| WO | | 2012058322 A1 | 5/2012 |

OTHER PUBLICATIONS

Office Action issued by SIPO in Chinese patent application No. 201510681273.1 dated Jan. 6, 2017—incl Engl lang transl.
The Office Action issued by the EPO in European Patent Application No. 16203726 dated May 16, 2019.
Extended European Search Report and Written Opinion issued in EP 11837027.9 dated Mar. 19, 2014.
First Examination Report issued in Australian patent application No. 2011319865 dated Dec. 6, 2013.
Office Action issued in Japanese patent application No. 2013-536784 dated Jul. 24, 2014.
Office Action issued in Chinese patent application No. 201180051973.2 dated Jul. 17, 2014.
International Report on Patentability issued in PCT/US2011/057906 dated May 10, 2013.

* cited by examiner

TISSUE DISPLACEMENT DUE TO FLANGE

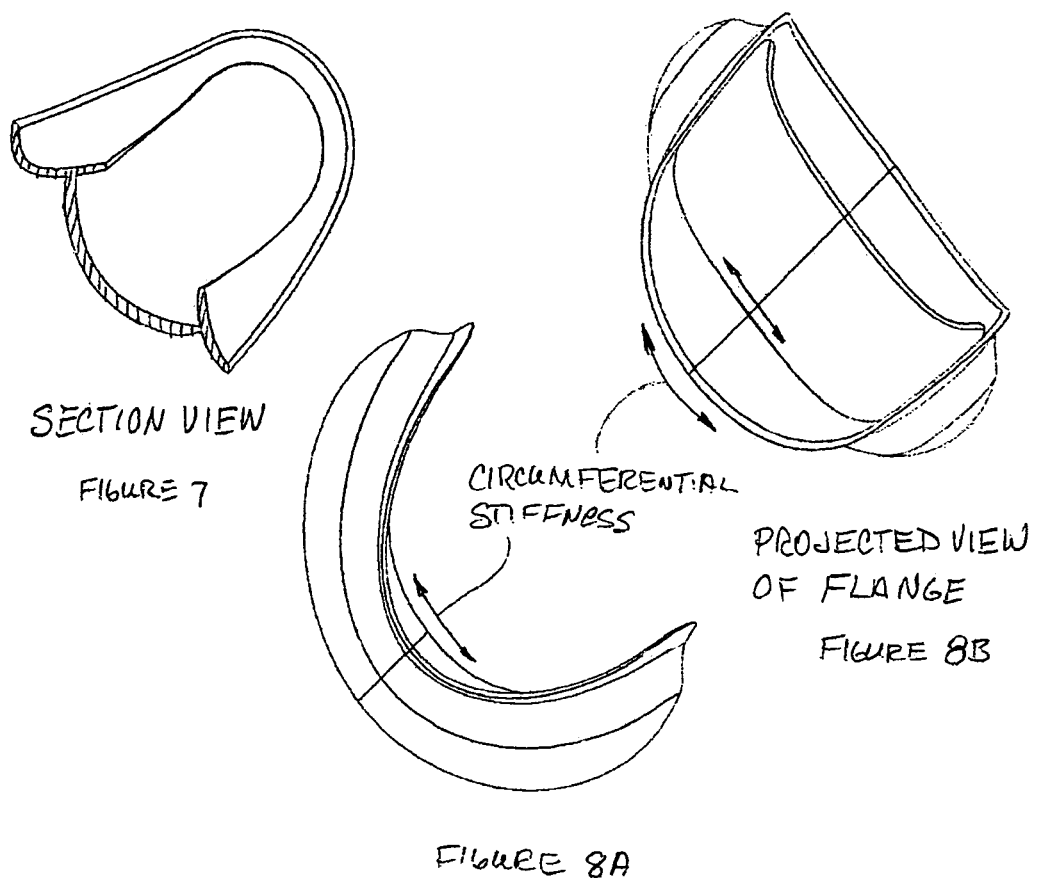

FRONTAL VIEW OF NP'K FLANGE

DEVICE AND METHOD FOR OPENING AN AIRWAY

The present invention is filed under 35 U.S.C. § 371 as the U.S. national phase of International Application No. PCT/US2011/057906, filed Oct. 26, 2011, which designated the U.S. and claims priority from U.S. Provisional Application No. 61/406,775, filed Oct. 26, 2010, which is hereby incorporated by reference in its entirety, including all tables, figures and claims.

BACKGROUND OF THE INVENTION

The following discussion of the background of the invention is merely provided to aid the reader in understanding the invention and is not admitted to describe or constitute prior art to the present invention.

The external application of negative pressure to patients for palliative or therapeutic purposes is well established in the medical arts. These "negative pressure" methods have in common a requirement for some apparatus to create and maintain the differential negative pressure (relative to atmospheric pressure for example) at the desired location on the patient.

In one example, "negative pressure wound therapy" ("NPWT"), also known as topical negative pressure, sub-atmospheric pressure dressings or vacuum sealing technique, is a therapeutic technique used to promote healing in acute or chronic wounds, fight infection and enhance healing of burns. A vacuum source is used to create sub-atmospheric pressure in the local wound environment. A dressing, containing a drainage tube, is fitted to the contours of a deep or irregularly-shaped wound and sealed with a transparent film. The tube is connected to the vacuum source, turning an open wound into a controlled, closed wound while removing excess fluid from the wound bed to enhance circulation and remove waste. As noted, NPWT has been used to treat both acute and chronic wounds, including diabetic foot ulcers, decubitus ulcers, surgical wounds, burns, traumatic wounds, etc.

In another example, external negative pressure may be applied to patients for purposes of maintaining or enhancing patency of the upper respiratory passages (referring to the nasopharynx, oropharynx, hypopharynx, and larynx). A therapeutic appliance is provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage, thereby providing a chamber (e.g., a hollow space filled with air molecules) lying between the surface and the throat. The appliance is configured to fit under the chin of a subject adjacent to the subject's throat at an external location corresponding approximately with the subject's soft tissue associated with the neck's anterior triangle. The therapy appliance is operably connected to an air pump which is configured to produce a partial vacuum in this chamber by removal of at least a portion of the gas molecules in this volume. Such methods and apparatuses may be used to support airway patency, for example, in patients with sleep apnea, airway tumors, inflammatory or traumatic damage to the upper respiratory passages, during surgery or sedation, to assist in intubations, extubations, aerosol delivery of drugs to the pulmonary tract, etc.

SUMMARY OF THE INVENTION

It is an object of the present invention to provide devices and methods for assisting in establishing a region of negative pressure on an external portion of a subject.

In a first aspect of the invention, an apparatus is provided that is configured to seat against the chin and neck of a patient to define a space-filled chamber between an inner surface of the apparatus and the skin of the user at an external location approximately at the soft tissue of a patient associated with the anterior triangle of the neck. The apparatus is adapted to maintain or increase patency of the upper airway by applying a vacuum-derived force to a surface of the neck of the patient when a therapeutic level of negative pressure is applied within the chamber, wherein the apparatus is sufficiently rigid to withstand the therapeutic level of negative pressure within the space.

In various embodiments, the apparatus comprises a flange attached to the apparatus edge which, when the apparatus is seated against the patient, is positioned to contact the patient's skin around at least a portion of the periphery of the apparatus. The flange is attached at its midregion to the apparatus edge by a pivoting member, said pivoting member configured to provide movement of the flange relative to the apparatus edge in order to allow the flange to adjust the skin contact surface of the flange to the contour of the patient's skin. This apparatus may be operably connected to an air pump in order to produce the desired negative pressure within the chamber. The flange may be formed as an integral part of the apparatus edge (e.g., moulded in a continuous fashion during production of the apparatus), or may be joined in a replaceable fashion (e.g., by providing a joining system on the flange and on the apparatus which may be pressed, snapped, zipped, etc. together to form the completed apparatus).

In certain embodiments, the apparatus comprises a peripheral edge configured to contact the skin of the user in order to enclose the chamber; and a supporting member positioned inward from a subregion of the peripheral edge which positions proximate to the patient's chin (i.e., the central forward portion of the lower jaw), the supporting member providing registration of the apparatus on the patient's chin.

Load forces from pressures lower than ambient pressure (e.g., a partial vacuum) within the chamber are carried by the apparatus and imparted on the user's skin through the edge of the apparatus and, in certain embodiments, by the supporting member providing registration of the apparatus on the patient's chin.

In order to improve compliance, comfort, and wear characteristics, the flange may comprise a nonlinear transverse profile over at least a portion of the flange in an unloaded state. This nonlinear transverse profile is configured to provide improved force distribution, relative to a linear transverse profile, when the apparatus is seated against the patient and the negative pressure is applied within the chamber. The nonlinear transverse profile may be, for example, concave or convex relative to the patient's skin. This is not meant to be limiting.

Alternatively, or together with this nonlinear transverse profile, the apparatus may comprise a breathable material inherent in, or positioned on, all or a portion of the skin contact surface of the flange, wherein the breathable material is configured to provide a controlled flow of air through the breathable material and into the chamber when the therapeutic level of negative pressure is applied within the chamber. Inclusion of such a breathable material can reduce accumulation of heat and/or moisture within the chamber.

As noted, the breathable material may be an inherent structure of the flange material. For example, the tooling used to form the flange (e.g., a mould) may provide a roughened or microchanneled surface to a portion of the flange which contacts the wearer's skin. As an example, the textured surface may comprise features having a depth from about 0.0005 inches to about 0.020 inches. Alternatively, the breathable material may comprise a separate porous material which may be joined in a replaceable (and therefore potentially disposable) fashion (e.g., with an adhesive strip). Examples of suitable breathable materials are described hereinafter. Preferred breathable material provides a controlled airflow rate greater than about 0.1 liters per minute (LPM), in certain embodiments between about 0.1 and about 56 LPM, and in other embodiments between about 0.1 and about 10 LPM, in each case when the apparatus is under a therapeutic level of negative pressure.

In another alternative, or together with one or both of the foregoing, the apparatus may comprise a low friction material having a coefficient of friction of about 0.65 or less, and in certain embodiments about 0.5 or less, on all or a portion of the skin contact surface of the flange, wherein the low friction material is configured to provide local movement of the flange relative to the skin surface.

In another alternative, or together with one or more of the foregoing, the apparatus may comprise a tacky material at an edge thereof, and preferably positioned on the patient contact surface of the flange. A "tacky material" as that term is used herein refers to a material which requires a measurable separation force for removal, e.g., of the flange from the patient's neck. Various standard test methodologies (e.g., ASTM D3121-94 or ASTM D2979-95) are known in the art for measuring tack of an adhesive material.

In another alternative, or together with one or more of the foregoing, the apparatus may comprise a peripheral edge configured to contact the skin of the user in order to enclose the chamber, wherein all or a portion of the wearer contact surface of the edge comprises a fluid-filled enclosure (e.g., in the form of a fluid filled tube). As used herein, "fluid-filled" is intended to include materials which are fluids (including without limitation liquids and gasses), gels, foams, waxes, flowing particulate solids, etc., which provide a compliant patient contact surface on the apparatus when a negative pressure is applied within the chamber. This fluid-filled, compliant material can assist in both sealing and comfort of the apparatus in use. The fluid filled enclosure can be separated intro zones circumferentially and/or radially around the contact surface of the apparatus to prevent migration of the filling to lower pressure areas within the enclosure. In the case where there are multiple zones, the zones may be configured to provide independent levels of resistance to loading. This resistance may be adjusted during manufacture, or controlled during use as desired. In addition, certain areas of the apparatus, such as the peripheral edge proximate to the chin, may lack the fluid-filled enclosure in order to more positively position the apparatus in registration zones.

In certain embodiments, the apparatus is configured to seat against the chin and neck of a patient to define a chamber at an external location approximately at the soft tissue of a patient associated with the anterior triangle of the neck. In these embodiments, the apparatus is adapted to maintain patency of the upper airway by applying a vacuum-derived force to a surface of the neck of the patient to draw the surface into the chamber when a therapeutic level of negative pressure is applied within the chamber.

In other embodiments, the apparatus is configured to seat against the skin of a patient to define a chamber at an external location overlying a wound.

A variety of additional elements may be provided in the apparatus of the present invention. These elements may include one or more of the following:

(i) flexural elements located within the flange configured to reduce longitudinal stress within the flange;

(ii) a radiused flange edge over at least a portion of the flange;

(iii) a variable thickness across the flange in a tangential direction, preferably with a minimum thickness at the edge of the flange; for example, the flange thickness may vary from a maximum thickness of between about 0.4 inches to about 0.1 inches, and a minimum thickness of about 0.02 inches or less. In certain embodiments, the maximum thickness is between about 0.312 inches and about 0.25 inches, and the minimum thickness is between about 0.01 and about 0.005 inches. The measurements are exclusive of any additional structures or coatings which may be reversibly applied to the flange.

(iv) an air pump connected to the apparatus via a hose or tube;

(v) an air pump which is wearable by the patient and is self-powered (that is, does not require connection to mains power for operation);

(vi) an air handling system which controls temperature, humidity, and air flow within the chamber.

(vii) an integral sealing member external to the flange which forms an enclosed air channel around all or a portion of the apparatus edge;

(viii) when the apparatus is adapted to maintain patency of the upper airway, a subregion of the apparatus edge which is proximate to the patient's chin which does not comprise the low friction material;

(ix) in the a subregion of the apparatus edge which is proximate to the patient's chin, a supporting member positioned inward from the apparatus edge which is configured to mate with the patient's chin; and (x) an integral sealing member underlying all or a portion of the skin contact surface of the flange, wherein the interface between the sealing member and the flange provides a low friction region configured to provide local movement of the of the flange relative to the skin surface. In these embodiments, a lubricating fluid may be placed between the sealing member and the flange to reduce friction at the interface.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE FIGURES

FIG. 7 depicts a section view of the apparatus showing the lower flange having a concave profile.

FIG. 8 depicts various projection views depicting the effect of circumferential stiffness on the shape of the apparatus.

DETAILED DESCRIPTION

External Negative Pressure Therapy Appliances

Figure 1:
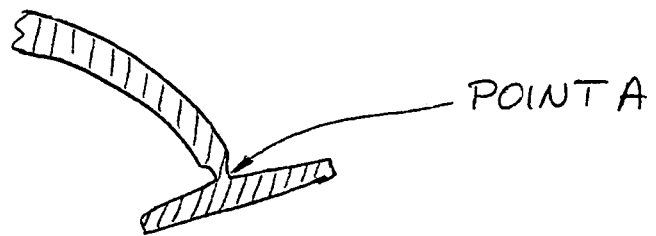
FIG. 1 and two depict cross sectional views through the apparatus at the level of the patient contact area. As depicted, the flange-to-apparatus connection point can be configured as integral to the apparatus body (FIG. 1) or as a reversibly attached component (FIG. 2).

The minimal design for a negative pressure therapy appliance is a structure configured to provide a space-filled chamber between an inner surface of the appliance and the skin of the user, where the structure is sufficiently rigid to withstand a desired partial vacuum created within the space; and to provide a peripheral rim that seals to the skin of the user in order to enclose the chamber. A vacuum in the range of about 7.62 to about 60.96 cm $H_2O$ is applied to a skin surface area of about 32.90 $cm^2$ to about 210.58 $cm^2$ in order to apply the desired therapeutic level of vacuum. These external therapy appliances have typically required a port connecting the enclosed space to an external vacuum source and power supply in order to achieve the desired therapeutic benefit for an entire treatment period.

A. The Therapy Appliance

The therapy appliance of the present invention comprises a structural member that provides a chamber between an inner surface of the appliance and the skin of the throat, where the structure is sufficiently rigid to withstand the required partial vacuum created within the space, and a peripheral rim that seals to the skin of the user in order to enclose the space. The vessel may be formed, molded, or fabricated from any material or combination of materials. Non-limiting examples of such materials suitable for constructing the therapy appliance include plastics, metals, natural fabrics, synthetic fabrics, and the like. The appliance may also be constructed from a material having resilient memory such as silicone, rubber, or urethane.

The only limitations on material(s) used for manufacture of the therapy appliance is that the appliance must be nontoxic (or "biocompatible," as it is in contact with the skin), and must be sufficiently rigid to maintain the space while carrying the desired partial vacuum load. The durometer or hardness is a unit of a material's resistance to indentation. The durometer of common materials is provided in the following table:

| Material | Durometer | Shore Scale |
| --- | --- | --- |
| Bicycle gel seat | 15-30 | OO |
| Chewing Gum | 20 | OO |
| Sorbothane | 40 | OO |
| Rubber band | 25 | A |
| Door seal | 55 | A |
| Automotive tire tread | 70 | A |
| Soft skateboard wheel | 75 | A |
| Hydraulic O-Rings | 70-90 | A |
| Hard skateboard wheel | 98 | A |
| Ebonite Rubber | 100 | A |
| Solid truck tires | 50 | D |
| Hard Hat | 75 | D |

The peripheral contact surfaces of the therapy appliance may be made of a softer, more compliant material than the structural regions of the appliance. A reduction in durometer to between 15 and 30 (Shore OO; roughly the hardness of chewing gum or rubber band) can permit the contact surface to better fill the contours of the skin. Numerous semi-cured or uncured rubbers having an almost gel-like consistency are known in the art. In the case of materials which in and of themselves do not have sufficient structural characteristics (e.g., ELASTOSIL® P 7616-160 A/B RTV-2 rubber, Wacker Chemie), the material may be encased, e.g., using a thin bladder (such as 1 mm polyurethane). These materials may be joined to the structural regions of the appliance in a 2-part molding process.

All or a portion of the contact surface of the therapy appliance may provide a tacky material which improves adhesion of the appliance to the wearer's skin. This tacky material may be formed as an integral part of the appliance, or as a material that is replaceable by the user. Certain pressure sensitive adhesives ("PSA's") come in many forms such as acrylic, silicone, rubber and hydrocolloid adhesives. The standard ways to classify adhesive strength is a 90 degree coupon peel test per PSTC or ASTM methods. Pressure sensitive adhesives in the range from 0.2 to 2.0 pounds per lineal inch are ideal. Excessive strength result in adverse affects associated with apparatus removal. Preferred materials include RTV silicones such as ELSATOSIL® (Wacker Silicones), including ELASTOSIL® P7671 A/B or SILPURAN® 2120 A/B. Such materials are biocompatible, sterilizable by gamma irradiation, and the tackiness may be controlled by varying the amount of catalyst added to the vulcanizing reaction. RTV-2 elastomers are two-component products that, when mixed, cure at room-temperature to a solid elastomer, a gel, or a flexible foam. RTV-2 is cured by mixing two components A and B. Through incomplete curing, the silicone rubber material remains soft and tacky.

Because the contact surface of the appliance applies a force to the user's skin (which may be perceived by the user as pressure against the skin) due to the forces generated by the therapeutic vacuum, a lack of comfort may result in a failure to use the appliance. Under certain circumstances, the capillaries, arterioles, and venules in the skin underlying the edge or lip may also collapse under prolonged use. Thus, the present invention describes several technologies that can enhance the comfort associated with using negative external pressure (cNEP) therapy. While the following discussion focuses on devices for maintaining or enhancing airway patency, the skilled artisan will understand that these concepts are generally applicable to negative pressure devices.

A. Flange to Dome Joint and Shape

Figure 20:
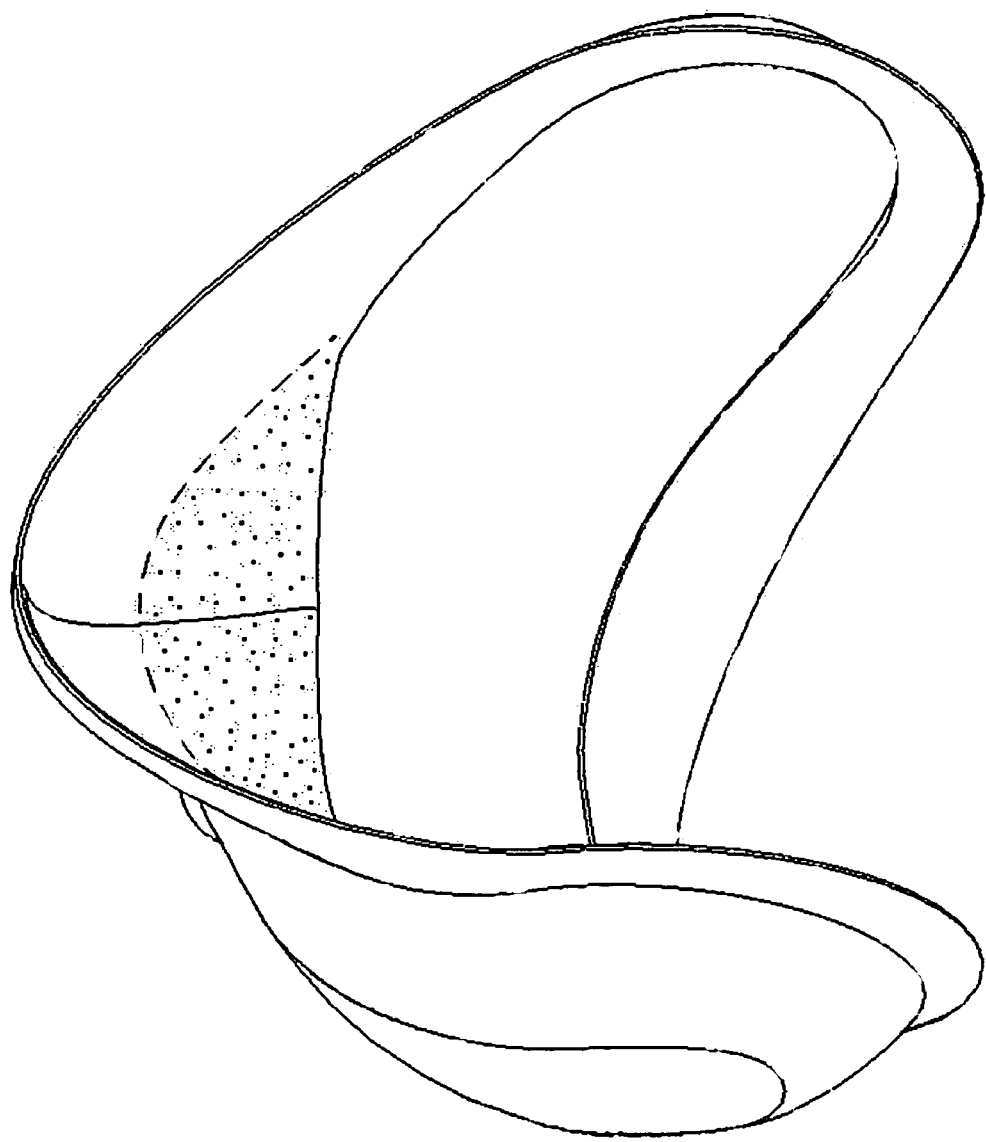
FIGS. 20 and 21 depict an embodiment of the apparatus of the present invention comprising a cup-shaped registration element to assist in proper placement of the apparatus by registering the apparatus on the wearer's chin.
Figure 21:
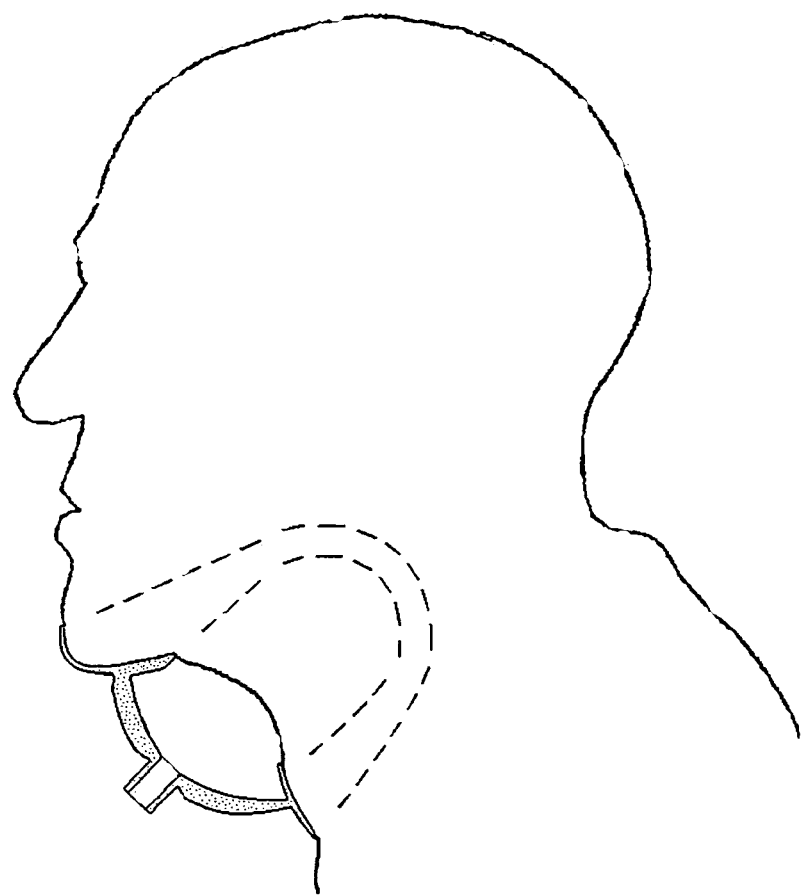

The apparatus is preferably made of a soft and compliant material, albeit one that is regionally of sufficient stiffness so as to withstand a therapeutic level of vacuum without collapsing. Due to a wide range of anatomical shapes, several apparatus sizes and shapes may be necessary. To make the user feel the apparatus is securely positioned, the apparatus is designed to intimately register with the mandible by provision of a registration element ("shelf") which rests under the chin. A "cup" shaped region which received the chin is formed by the edge of the apparatus and this shelf, as depicted in FIG. 20 (dotted region). The chin cup formed thereby can provide a visual feature that helps ensure proper placement of the collar onto the chin as depicted in FIG. 21. Additionally, by imparting a portion of the load created at the apparatus/patient interface onto the relatively rigid structure of the chin, improved leverage can be gained on the soft tissue overlying the pharynx which is sought to be moved.

Figure 2:
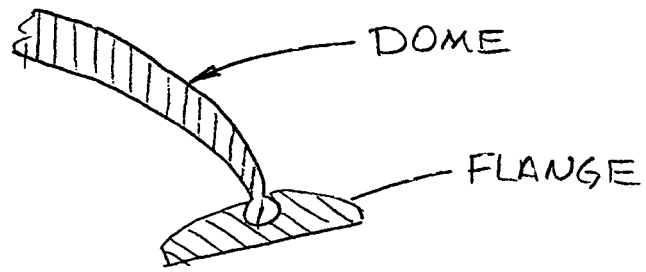

Advantageously, the flange areas near ear and neck are constructed to be compliant and self-aligning to the anatomy of the wearer. FIG. 1 depicts a transverse section through the dome and flange. In this figure, the flange is depicted as integral to the apparatus edge. The juncture shows a very thin section at point A, which is approximately at the midpoint of the flange contact surface with the skin. This thin section is very weak and allows the flange to pivot freely. This is advantageous as areas of high contact pressure due to flange misalignment with the neck are reduced. FIG. 2 shows alternative embodiments of the design in which the flange is reversibly attached to the apparatus edge by a snap-in joint.

A properly aligned flange can still impose high contact pressure points unless it is designed to address the behavior of the tissue beneath it. The primary characteristic of human tissue that is important is its compressive stiffness. This term varies with the thickness of tissue captured between the apparatus and very stiff structure such as bone or cartilage. Individuals with extra fatty tissue will have a less stiff or softer system. In traversing the periphery of the apparatus flange, the tissue stiffness varies associated with skin toughness and underlying substructure. Relative compressive stiffness may therefore vary from one anatomical region to another, and exhibit individual user variation. Comfort is the absence of pain. Pain is incurred by high contact pressure over time. The actual offending area can be very small; it can be an edge or even a point.

Figure 3:
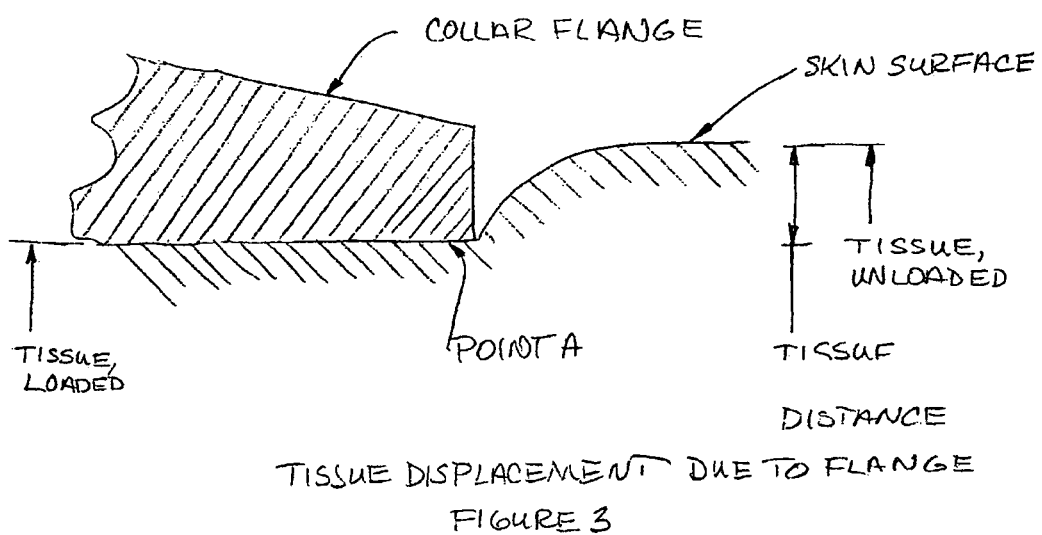
FIGS. 3 and 4 schematically depict force loading at the patient contact area of the apparatus when in use.
Figure 4:
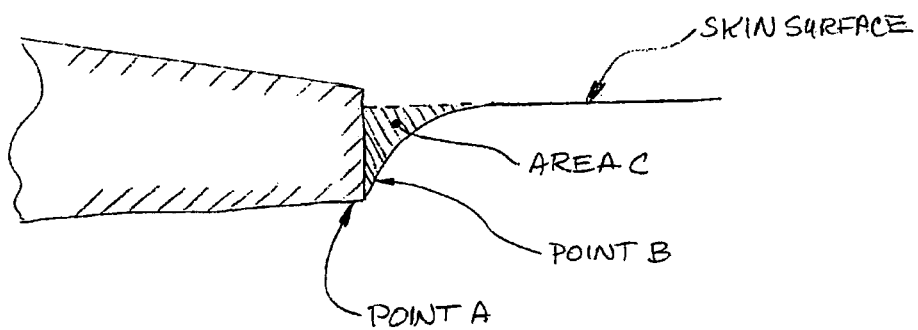

FIG. 3 shows an enlarged view of the apparatus flange loaded on to human tissue in a typical fashion. The unloaded flange is designed with a nonlinear transverse profile that bends distal to the apparatus. The loaded shape of the flange is established on the basis of load, material properties, width and human tissue properties. The shape of the loaded flange (in reference to flat human tissue) is preferred to be approximately flat for the central 80% of the flange and curved upward for each 10% edge condition. When load from the dome of the apparatus is applied to the flange, the distal ends of the flange flex back and become straight. For purposes of clarity, a cross-section view of the flange will show the contact surface as straight. In reality, straight means to follow the anatomical curves of the body. It also maintains the structure under the flange is skin, muscle/fatty tissue and bone respectively and that this structure possesses a nonlinear spring rate behavior. Therefore uniform compression of the tissue structure will yield uniform contact pressure. However due to the structural cohesiveness of the tissue, a flange edge condition exists that imparts higher stress on the tissue. This is denoted as point A. FIG. 4 shows an area C. This is the potential energy associated with compressing the tissue as associated with the natural curvature of the skin surface. The displaced tissue of the natural curve translates to a tensile term at point B.

Figure 5:
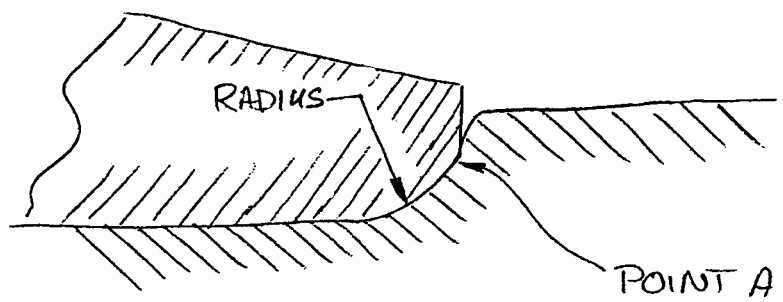
FIG. 5 schematically depict the effects of an alternative flange shape (a radiused edge) on force loading at the patient contact area of the apparatus when in use.

This load is carried under the flange and the tissue will feel the addition. The total stress imparted in or on the skin is the vectorial sum of the compressive stress and the lateral tensile stress. FIG. 5 shows a flange edge design that includes a radiused edge. This radius reduces the peak stress in two ways; first, the potential energy area highlighted in FIG. 4 is reduced and the contact pressure term is less at Point A. The ideal solution is to select the smallest radius that will yield a flange edge total stress condition that matches the nominal stress within the central regions of the flange. The variables considered in designing the ideal radius include, for example, anatomical shape and thickness of tissue. Based on direct measurement, the flange edge radius advantageously varies from 0.02 to 0.25 inches. Additionally, the radius may preferentially be tangential with the skin contact surface of the flange and the center point located 70 percent of the radius value from the flange edge. While this design is a simple radius, other embodiments can offer benefit. They may take the form of a bevel or any mathematical expression that depicts a curve from the flange surface to the edge.

Figure 6:
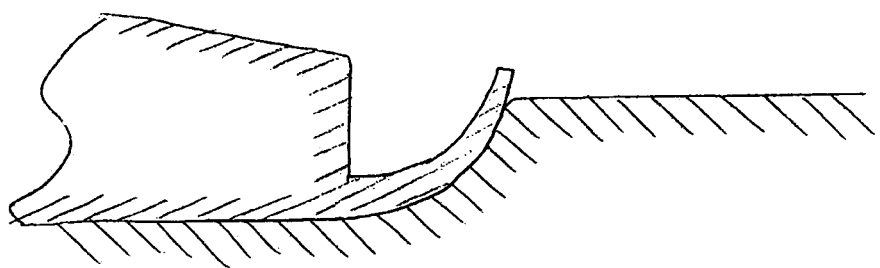
FIG. 6 schematically depict the effects of an alternative flange shape (a cantilevered lip) on force loading at the patient contact area of the apparatus when in use.

FIG. 6 shows a design where the desired radiused curve is established by cantilever flexing of a thin lip of silicone material or the like. The feature may or may not be integral with the apparatus and/or flange. The advantage of the design is the thin lip in the unloaded state is curved distal to the apparatus. This inherently maintains an effective seal against air leakage.

Figure 9A:
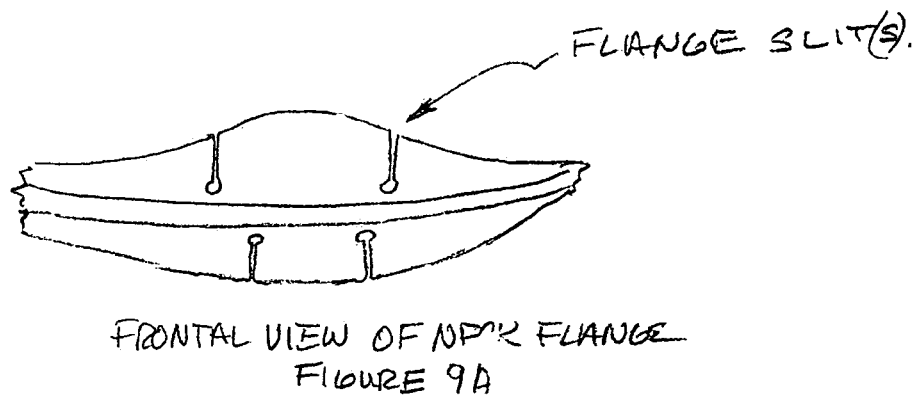
FIG. 9 depicts various embodiments to reduce the circumferential stiffness of the apparatus.
Figure 9B:
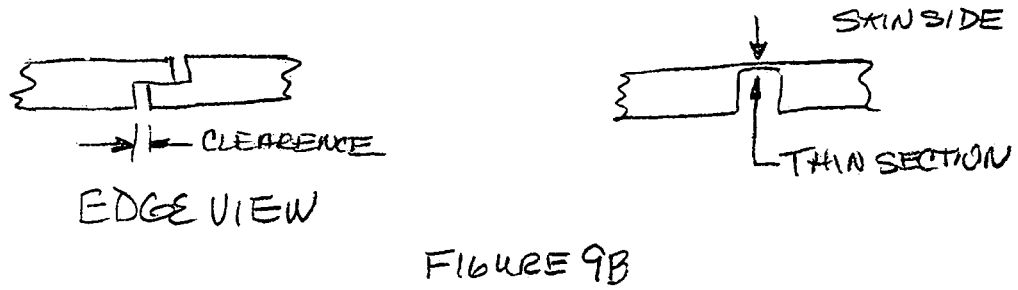

B. Methods to Reduce the Negative Effects of Longitudinal (Circumferential) Stiffness The lower flange of the apparatus that crosses in front of the neck is curved to match the shape of the neck. This curvature inhibits the flange from self aligning with the neck. When the flange attempts to pivot, the circumferential length of the top and bottom edges of the flange would respectively have to lengthen and shorten. Since the material is relatively stiff it simply inhibits the alignment. FIG. 7 is a section view of the apparatus showing the lower flange having a concave profile, and the rotational pivot point. FIGS. 8A and 8B is a two projection view of the flange. It shows the stretching and bunching of flange edge material. FIG. 9A shows methods to reduce longitudinal (circumferential) stiffness by adding discontinuities in the form of local slits. The slits are orientated normal to the flange length and therefore do not influence the beneficial load distribution characteristics of the flange. FIG. 9B shows alternative embodiments.

C. Conditioning the Air within the Apparatus

Sleep apnea is a chronic condition that requires continuous therapy during sleep. The apparatus will enclose regions of the neck, which may tend to feel hot and moist to the user. These uncomfortable conditions may drive the user to attempt to relocate the apparatus leading to air leakage and general increase in arousals from sleep. Promoting air flow through the apparatus will help mitigate the negative effects of moisture and temperature especially in applications where the apparatus is worn for long periods of time.

Figure 10:
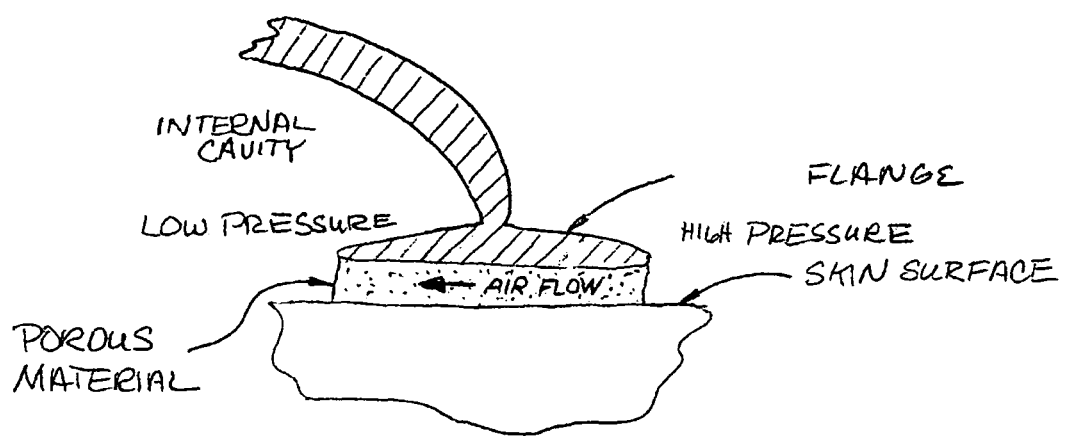
FIG. 10 depicts the use of a vent layer to control levels of heat and humidity which can accumulate within the apparatus when in use.

FIG. 10 is a sketch of a vent layer that promotes outside air to flow across the seal flange and into the apparatus cavity. The vent layer is made of biocompatible semi-porous material that has sufficient structure to resist collapse thereby maintaining air passage. Not only is the material to provide an air conduit into the apparatus but also provide air access to the skin such that free exchange of gasses and moisture can occur. This can serve to mitigate skin injury caused or worsened by heat and humidity. The preferred airflow rate through the apparatus is greater than about 0.1 standard cubic feet per minute (LPM), in certain embodiments between about 0.1 and about 56 LPM, and in other embodiments between about 0.1 and about 10 LPM. Typical materials may be foams, woven cloths and nonwoven layups. In the case where the apparatus flange is specifically designed to minimize peak tissue contact pressures, the vent must be thin so as to not negate the flange effectiveness. Air flow rate can be varied based on the flow characteristics of the material chosen. For example, reducing the air path length by ½ should result in doubling of the flow rate; reducing the thickness of the material by ½ should halve the flow rate.

Figure 11A:
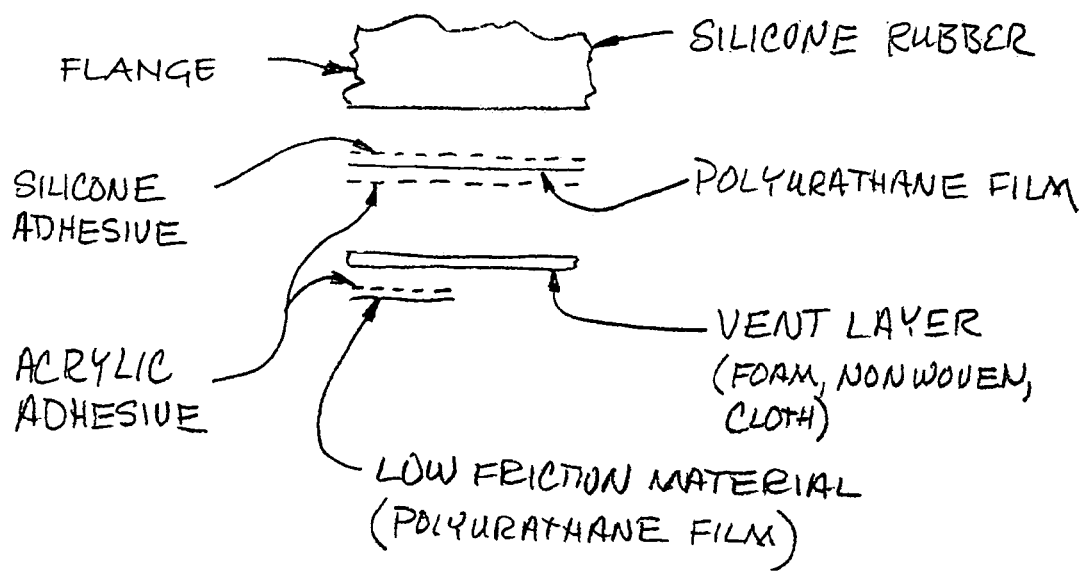
FIG. 11A depicts an embodiment in which the vent layer is formed from a lamination stack composed of materials.

Since this vent layer (liner) is in intimate contact with the skin, the product life may be limited to just a few days. This will benefit from a simple means to remove and reapply a new liner. Pressure sensitive adhesives are ideal for this application. The old liner is simply removed from the apparatus by pulling a special tab, thereby peeling the liner off. The new liner is applied by peeling off the backing paper, positioning the liner on the apparatus, and applying mild contact pressure. The liner may be constructed from more than just a single layer of porous material. It may consist of many laminated components. See, e.g., the exploded view in FIG. 11A. The apparatus is made of silicone rubber and thus may require special adhesives. A typical lamination stack would consist of; a vent layer, acrylic adhesive, polyurethane film, silicone adhesive and finely the apparatus. The acrylic adhesives should be stronger than the silicone adhesive to insure clean removal of the liner from the apparatus. Also, the silicone adhesive formulation must have greater adhesion to the polyurethane film than the silicone material of the apparatus.

Figure 11B:
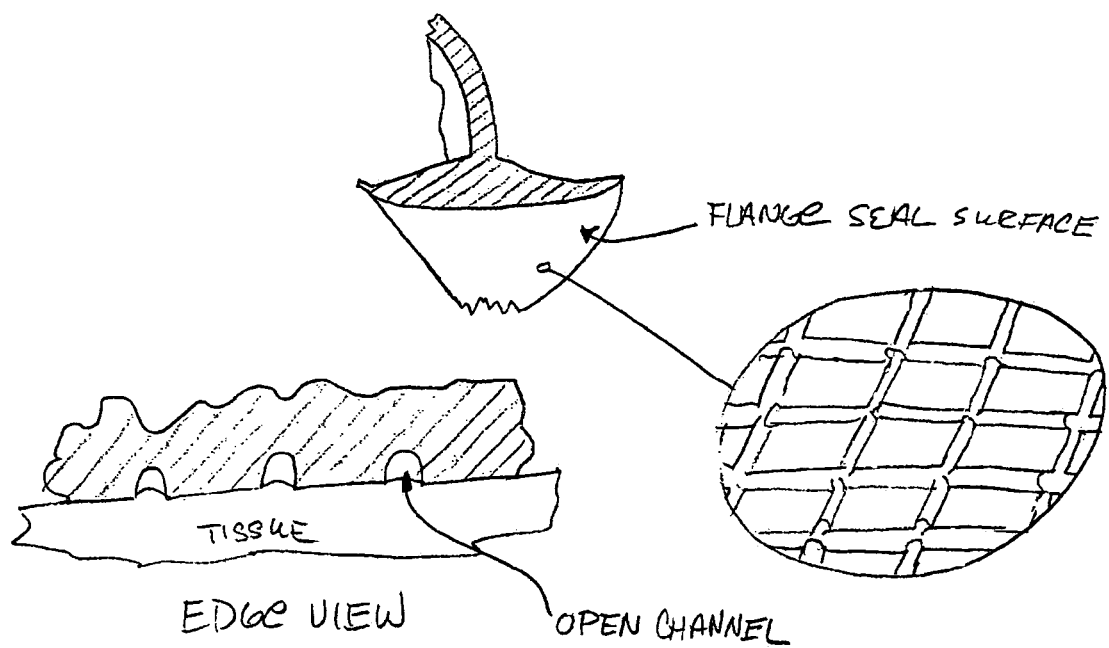
FIG. 11B depicts an embodiment in which a microchanneled surface is used as a component of a vent layer.

An additional layer of low friction material may also be applied to the vent layer of the liner in strategic areas to mitigate chaffing on the skin. Preferred locations will be discussed hereinafter. The following are examples of likely adhesives: 1. Acrylics 2. Silicone 3. Hydrocolloid FIG. 11B depicts another embodiment of ventilating the apparatus and seal area. In this case the skin contact side of the apparatus flange would contain a lattice of micro channels that provide a conduit for airflow. The aspect ratio of the channels would be sufficiently deep to prevent neck tissue from migrating to the bottom and blocking the airflow. Channel depth to width ratios may vary from 1 to 4. Channel width may vary from 0.0005 to 0.020. The flange surface area dedicated to the channel opening may range from 5 to 20 percent. The lattice would likely be configured in the injection mold tooling. Various techniques may be employed such as micromachining, chemical photo etching, or laser etching. Also secondary manufacturing process steps such as laser etching could be used on the apparatus flange directly.

Figure 12:
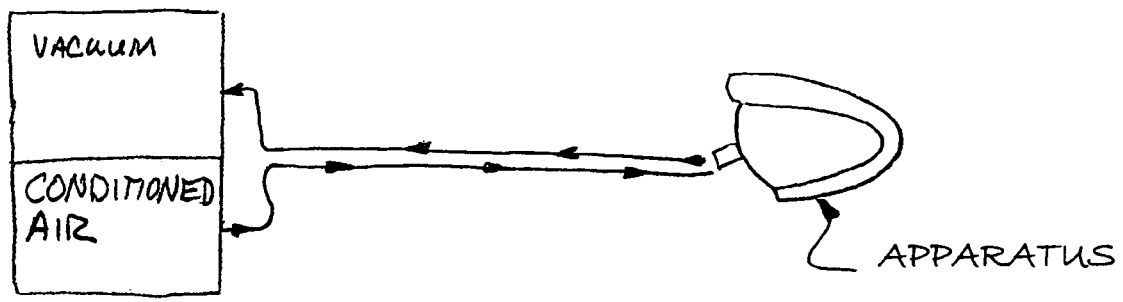
FIGS. 12 and 13 depict in schematic form a system for managing environmental quality in an apparatus of the present invention.
Figure 13:
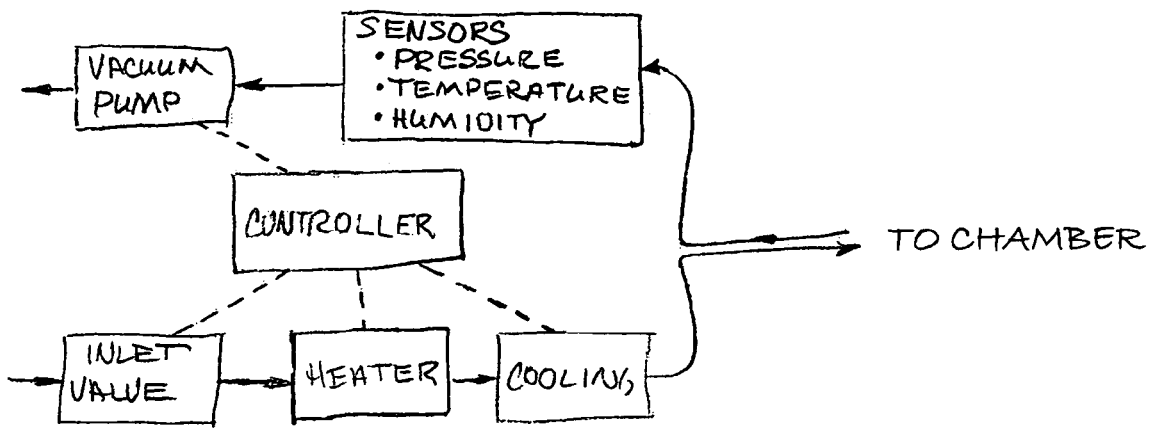

Simply drawing air across the flange may not be enough for some users. Conditioning the air in the apparatus may involve heating, cooling and controlling the humidity. FIG. 12 shows a system consisting of a dual line tubing, and an integrated vacuum and air conditioning unit. The system would meter conditioned air into the apparatus and exhaust air with the vacuum pump. The connecting tube may be two tubes in a sheath, integrally molded side by side, or concentric. FIG. 13 show a typical control scheme consisting of microcontroller, pump, inlet valve, heater, cooler, and pressure, temperature and humidity sensors. The microcontroller would compare sensor input 4 with target values and adjust the pump flow, inlet valve, heater and cooler accordingly. For example, to lower humidity and/or temperature the inlet valve would open increasing the air flow rate through the apparatus. Some individuals may like warm air when first going to bed. This could be done with electric heating or by utilizing the inherent heat caused by the pump and motor. Others may like additional cooling benefits that bring temperature levels in the apparatus below room temperature. The system would utilize solid-state thermoelectric (Peltier) cooling. In addition, a short duration maximum cooling feature could be incorporated that would cycle with every detected apnea event. Other means to reduce humidity may involve a closed air system circulated in the presence of a replaceable desiccant.

A two tube system that ports both the supply and exhaust in the central region of the apparatus is the simplest air flow system. Any apparatus design which requires higher air exchange rate, however, may drive the need for higher pump capacities. A more efficient design locates the supply and exhaust ports near the ends of the apparatus. Forced air currents will then traverse approximately 8 square inches of skin surface prior to exhausting the apparatus. This will maximize effectiveness in managing moisture and temperature.

Figure 14:
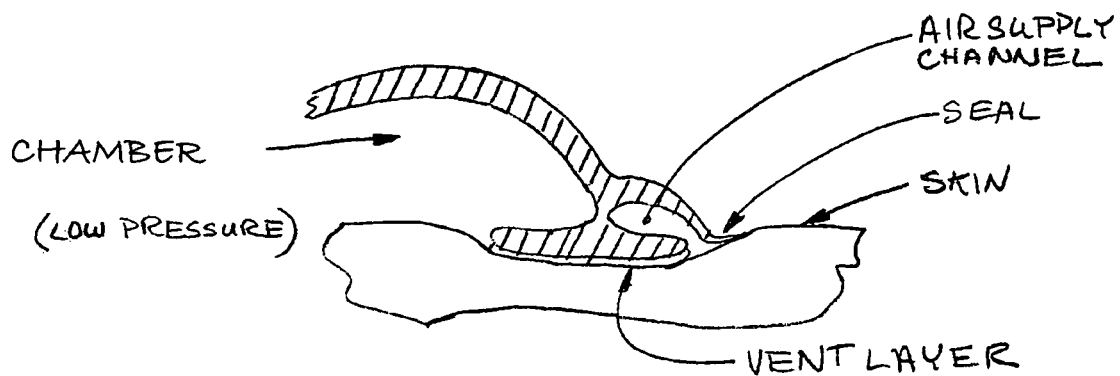
FIG. 14 depicts an alternative embodiment for managing environmental quality in an apparatus of the present invention.

FIG. 14 details a method that ports supply (conditioned) air to an annular channel that runs the complete periphery of the apparatus. The supply tube connection and the annular cavity are connected via integral cores in the apparatus or through external means. The advantage of this design is the conditioned air is forced under the flange. Since the flange area increases the total skin conditioning surface area by 30 to 50 percent the effectiveness is improved. The air supply annular channel is isolated from the outside by a lip seal.

Many thick vent materials such as foams are ideally suited to enhance comfort but may pass too much air. However, they can be used by controlling the airflow rate with a secondary device. A secondary device could be an orifice or control valve. The apparatus design would have a full or partial annular channel as depicted in FIG. 14. Air access to the channel would be controlled by one or more orifices or similar flow control device.

C. Apparatus Positional Stability and Friction Reduction

The apparatus when applied at therapeutic vacuums is securely held in position by the vacuum forces and the friction between skin and the silicone rubber material. The apparatus is preferably designed to match the profound shape of the mandible which causes the apparatus to follow natural head movement. While this establishes good positional stability, it is not favorable for the neck. When head/apparatus movement is greater than the flaccidity of the skin, sliding occurs. This causes chaffing and discomfort to the user.

Figure 15:
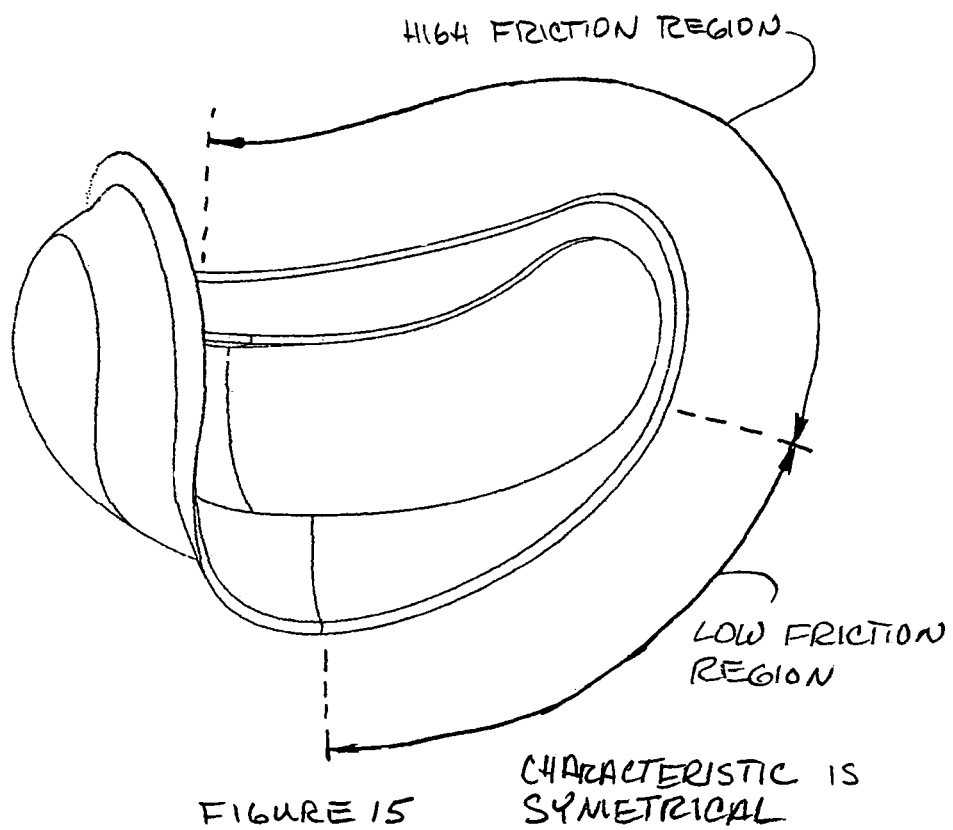
FIG. 15 depicts an apparatus of the present invention having regions of differing friction characteristics on the patient contact area of the apparatus.

There are two approaches described in this disclosure for avoiding such chafing; the first is to reduce the friction of the materials used in the neck region and secondly to eliminate neck sliding by decoupling the mandible and neck flanges. FIG. 15 defines the different regions on the flange that high and low friction characteristics can be utilized in optimizing apparatus positional stability and user comfort. While this is a single approach, there are numerous embodiments that can yield similar results. There are many materials that exhibit a wide range of friction properties. They include but not limited to woven fabrics, non-wovens, plastic films and adhesives. The table below is a limited listing of materials and their coefficient of friction properties against human skin.

| Material | Coefficient of Friction |
| --- | --- |
| Rip-Stop Nylon | 0.71 |
| Silk | 0.70 |
| Spandex, loosely woven | 0.69 |
| Spandex, tightly woven | 0.66 |
| Black spandex | 0.56 |
| Crinkle cotton | 0.69 |
| Cotton | 0.77 |
| Loosely woven chiffon | 0.56 |
| Tightly woven chiffon | 0.53 |
| Light weight cotton | 0.68 |
| Cotton(1) | 0.73 |
| Cotton(2) | 0.62 |
| Satin | 0.41 |
| Medifoam #30 | 0.81 |
| Neoprene soft side | 0.61 |
| Neoprene hard side | 0.55 |
| Laminate sample (1) | 0.74 |
| Laminate sample (2) | 0.67 |

For example Medifoam #30 placed in the mandible region and satin placed in the neck region offer good positional stability without neck discomfort. In addition the apparatus flange itself may be conditioned with secondary process to influence the coefficient of friction.

Figure 16:
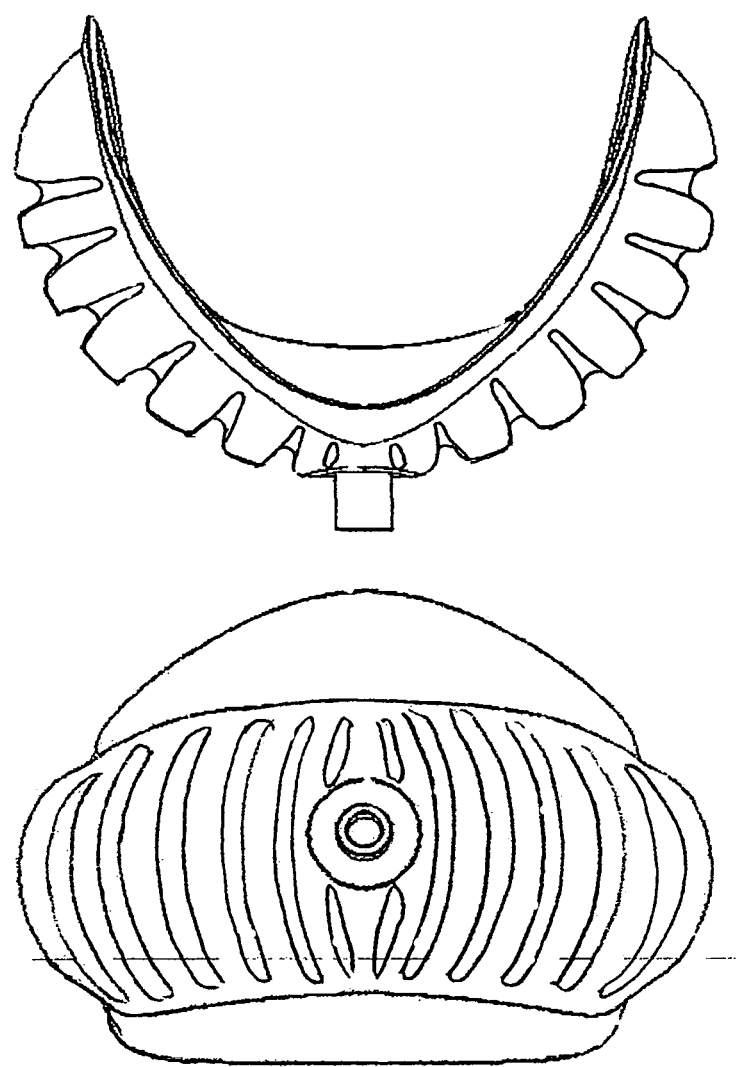
FIG. 16 depicts an apparatus of the present invention configured to provide modified shear forces during head movement.

FIG. 16 shows a method of apparatus construction that minimizes lateral forces the flange imposes on the neck with head sideways rotation. The current apparatus design incorporates a simple dome to effectively react vacuum forces. A simple dome creates a stiff relationship between the upper and lower flange in the lateral shear direction due to the material being substantially in plane. To reduce this, the section modulus properties need to be softened by adding vertical invaginations in the dome. The arch of the dome will be maintained to carry the vacuum loads.

Figure 17A:
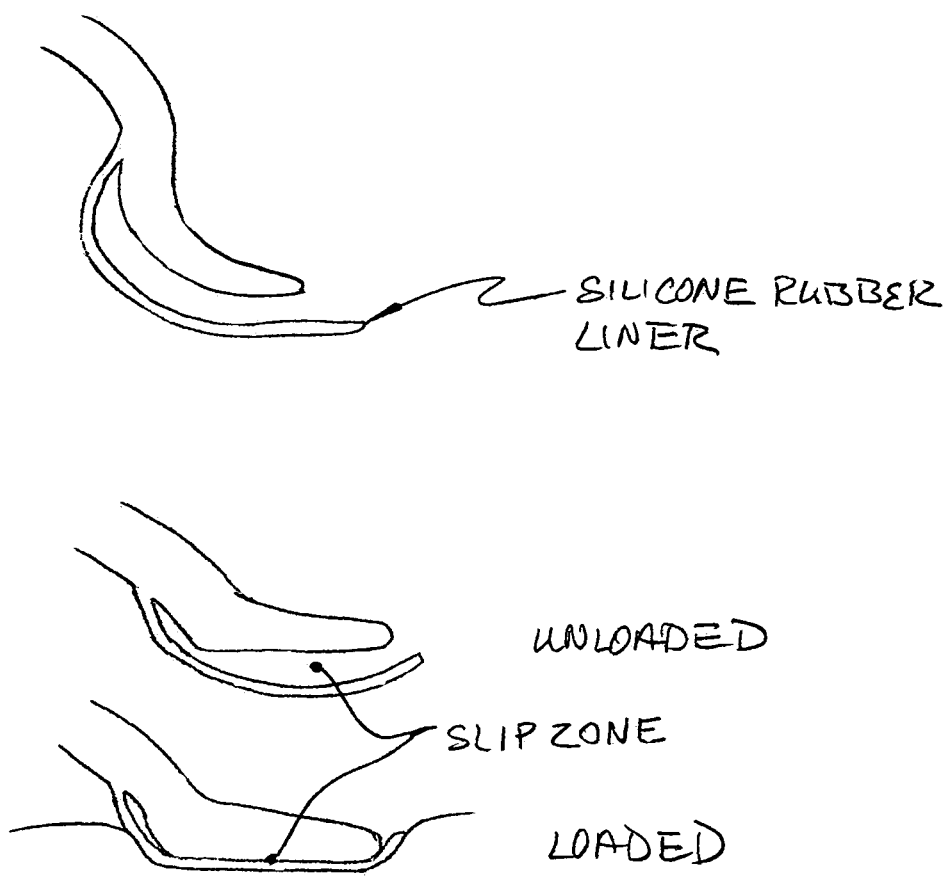
FIG. 17 depicts embodiments in which the patient contact area of the apparatus of the present invention is modified to control friction characteristics.
Figure 17B:
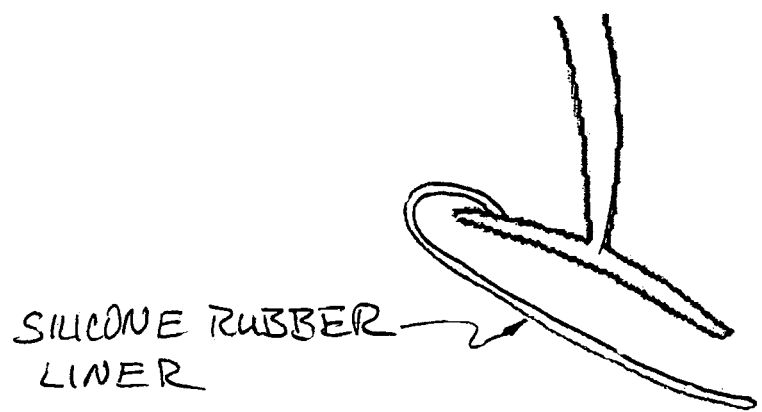

FIGS. 17A and B shows several images of an apparatus with an integrally attached thin film or membrane. This membrane is situated between the apparatus support flange and the user's skin and ranges from 0.004 to 0.032 inches thick. With head motion, the apparatus flange will move while the flexible membrane remains fixed with respect to the skin. This forces the relative motion to occur between the apparatus flange and the membrane eliminating abrasion marks on the user's neck. The coefficient of friction between the flange and the membrane is reduced by use of any conventional liquid, gel or dry film lubricant.

Figure 18:
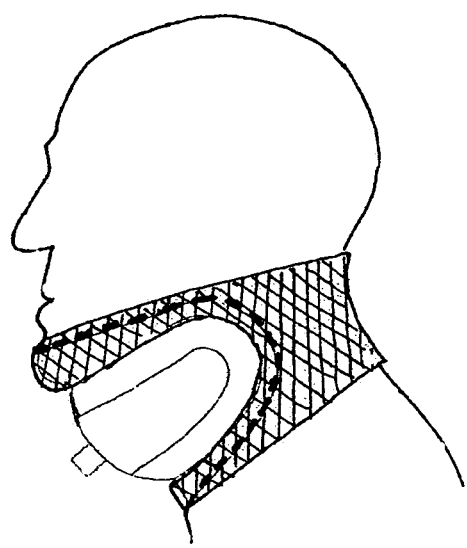
FIGS. 18 and 19 depict the use of a collar to secure the apparatus of the present invention to the user.
Figure 19:
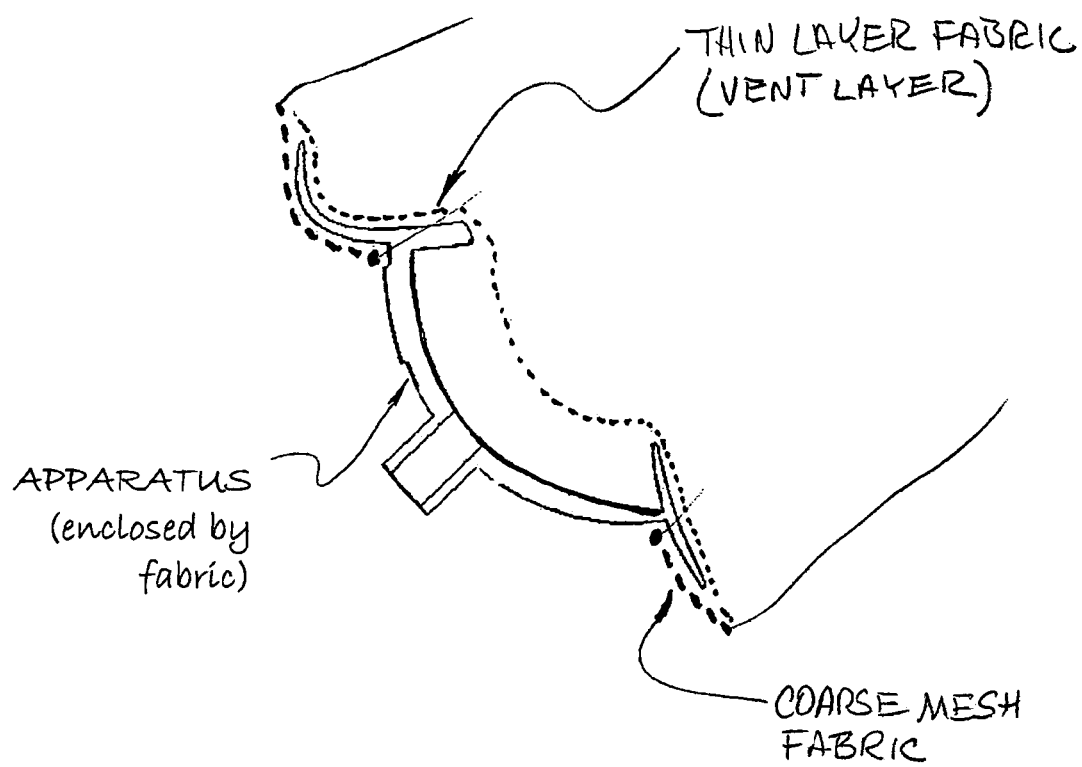

FIG. 18 shows a method to securely position the apparatus while providing a cloth vent layer between the apparatus flange and the user's skin. The outer fabric is a soft open weave mesh that promotes air circulation on the neck. It fastens in the back with snaps or Velcro tape. The inner fabric is the vent layer and likely thin cotton or similar. The inner layer is sewn to the outer fabric at the periphery of the apparatus. Additional material is tucked in the apparatus to provide clearance for tissue that enters the apparatus at vacuum. FIG. 19 depicts such an embodiment in cross section.

B. Creating a Partial Vacuum—the Air Pump

The term "air pump" as used herein refers to a device that removes gas molecules from a sealed chamber in order to leave behind a partial vacuum.

A vacuum may be created within the chamber formed by the appliance and the user's skin surface in a number of ways. A simple method is to manufacture the therapy appliance using a resilient memory-shaped material that may be compressed like a bulb, mated to the user's throat, and then released. In this case, when the appliance is mated to the throat and the appliance released, return of the appliance to its original shape creates a partial vacuum within the space.

A preferred powered design for a pump module utilizes a positive displacement pump, most preferably a diaphragm pump driven by either a linear motor, or a brushed or brushless DC rotational motor drive. In particularly preferred examples in which a linear motor is used, the linear motor is operatively linked to control circuitry configured to drive single discrete strokes of the pump as well as multiple strokes. In particularly preferred examples in which a DC motor is used, the motor is operatively linked to a controller configured to drive single discrete revolutions of the motor as well as multiple rotations. Examples of these and other suitable air pumps are described below.

Another preferred powered design for a pump module utilizes a disc pump as described in WO2009/112866, which is hereby incorporated by reference in its entirety. In such a disc pump, a main cavity is defined by end walls and a side wall. The cavity is preferably circular in shape, although elliptical and other shapes could be used. The cavity is provided with a nodal air inlet and a valved air outlet. The actuator comprises a piezoelectric disc attached to a disc. When an appropriate electrical drive is applied, the actuator is caused to vibrate in a direction substantially perpendicular to the plane of the cavity, thereby generating radial pressure oscillations within the fluid in the cavity. The lowest resonant frequency of radial fluid pressure oscillations in the main cavity is preferably greater than 500 Hz, and the frequency of the oscillatory motion may be within 20% of the lowest resonant frequency of radial pressure oscillations in the main cavity.

a. Air Pump Types

The term "positive displacement pump" as used herein refers to a mechanism to repeatedly expand a cavity, allow gas molecules to flow into the cavity from the chamber, seal off the cavity, and exhaust the gas molecules to the atmosphere. Of the "positive displacement" type of vacuum pumps there are preferred candidates: vane pumps and diaphragm pumps.

Vane pumps move gas through the pump using a rotating assembly in the pumping chamber that move the gas from inlet to outlet. As the rotor turns, the ends of the vane barely touch the housing, creating a seal from inlet to outlet. The gas is pressurized as the volume between the vanes lessens during one half-cycle and is suctioned through an intake port during the other half-cycle. Vane pumps create pressure pulses equal to the number of vanes contained within the pump and the speed at which the vanes are turned. The vane type pump does not maintain a vacuum throughout the pump circuit, and therefore the system would include a check valve between the pump and the enclosed partial vacuum chamber to prevent vacuum loss. Such pumps have very low starting torque and would be well suited for use with a DC motor. In comparison with other pumps, the noise frequency created will be higher and therefore may work well with sound abatement technologies described below.

Diaphragm pumps are popular for small to medium size applications as an alternative to vane pumps. Diaphragm pumps can be extremely low maintenance and quiet. Diaphragm pump function by mechanically moving a diaphragm which displaces air. A pair of one way valves is provided to direct the movement of air, thereby creating the vacuum. These valves will also provide the necessary function of sealing the pump circuit from the enclosed partial vacuum chamber.

Within this pump category there are several ways in which diaphragm movement is achieved. Linear pumps can connect the diaphragm directly to an armature and vibrate the armature in a linear direction. Motor control in this type of pump can be very simple. A linear motor driving a linear pump can move a diaphragm very slowly, which may be advantageous from the point of view of noise and vibration creation. Rotary diaphragm pumps stroke the diaphragm with a rotary to axial mechanical converter. They have low starting torque and can be coupled with DC motors. These pumps are inexpensive.

In another alternative, an air pump may be a dynamic pump such as a regenerative pump. In a regenerative pump, an impeller rotates, creating a centrifugal force which moves the air molecules from the blade root to its tip. Leaving the blade tip, the air flows around the housing contour and back down to the root of a succeeding blade, where the flow pattern is repeated. This action provides a quasi-staging effect to increase pressure differential capability. The speed of the rotating impeller determines the degree of pressure change. Such pumps are best used for external (e.g., tabletop) vacuum sources, as opposed to a vacuum source supported on the user as described herein.

A particularly preferred pump is a diaphragm pump having a single stroke displacement of between 0.001 and 0.01 $in^3$, and most preferably in the range of 0.003 to 0.005 $in^3$. A pump with a displacement of about 0.004 $in^3$ will yield a maximal evacuation rate of 12 $in^3$/min when driven at 3000 rpm using a rotary brushless DC motor or 60 Hz using a linear DC motor. This could completely evacuate an appliance enclosing a volume of between 0.5 and 2 $in^3$ in 2.5 to 60 seconds. Of course, complete evacuation of the chamber enclosed by the appliance is not required to generate a therapeutic level of vacuum. For example, in an appliance providing an 8 $in^3$ chamber, removal of about 1.6 $in^3$ can provide an appropriate working pressure. Thus, a full pumping mode of 1 to 25 $in^3$/min can quickly generate therapeutic vacuum levels within the appliance.

Following the initial evacuation, the air pump is driven only as needed to maintain the partial vacuum above the desired threshold. Assuming a leakage rate of air into the enclosed chamber at a rate of between 0.005 and 0.5 $in^3$/min, the diaphragm pump could be driven to pulse a single stroke only once every few seconds to few minutes. This dual evacuation/quiet mode approach has numerous advantages, including being extremely quiet and low in both vibration and battery consumption. For example, a preferred pump can run in quiet mode at a rate of between 0.005 and 0.5 $in^3$/min (most preferably at 0.01 and 0.1 $in^3$/min), which can remove between 2.4 and 240 $in^3$ of air in an 8 hour night. Given a pumping rate of 5 strokes a second and a pump displacement of 0.004 $in^3$/stroke, such a pump could run 0.25 to 25 seconds out of each minute and still deliver the desired performance.

b. Electric Motor Types

This application requires both slow and fast operation, low sound production, and efficient battery usage. In a DC motor, when the motor is provided with its rated voltage, the motor operates at full rpm. To control speed, one must turn the motor off for a short period of time. This motor voltage is provided typically as a square wave. The frequency of this square wave is typically very fast (optimally in a range of from 2,000 to 18,000 Hz), and the amount of power the motor receives is proportional to the percentage of time the square wave is "on" versus "off." This technique is called pulse width modulation (PWM). PWM accommodates the slow motor speed operation required of the "quiet mode" as short pulses of full voltage create strong magnetic fields that force highly controlled partial rotations. Running in the very slow speed range may require the addition of an encoder to provide feedback to a controller for accurate speed control.

C. Vacuum Control

Vacuum control may be provided by both mechanical and/or electronic control mechanisms. A simple mechanical mechanism to control the vacuum within the appliance chamber is to provide a miniature vacuum relief valve press fit into a port in the appliance. The relief valve is selected to admit air when a preselected vacuum level is exceeded. The air pump is then driven at a constant speed, with the vacuum release valve controlling the partial vacuum by opening when the vacuum exceeds a desired level and closing below that level. Preferred operational vacuum levels are selected within a range of between about 7.6 cm to about 61 cm of water by inserting an appropriate vacuum relief valve to eliminate undesirable over-pressure conditions above a predetermined range. No monitoring of internal vacuum or control of the motor driving the air pump is necessary in this embodiment. However, this embodiment would tend to provide unnecessary noise and to use battery power at a potentially undesirable rate. A preferred electronic/mechanical vacuum control mechanism may comprise a microcontroller coupled to a vacuum or pressure sensor, motor control circuitry, and a battery pack module.

Numerous optional components can be employed to improve the performance and control of the device. For example, because the volume enclosed by the appliance and the user's skin is approximately known, the time to achieve the partial vacuum can be calculated. The vacuum or pressure sensor detects a drop in vacuum that requires energizing the pump and motor. If it is determined that the partial vacuum has not been achieved in some appropriate time, the vacuum source can be deactivated, and optionally an alarm condition indicated. Suitable alarms can include visual (e.g., a light), auditory (e.g., a tone), and/or tactile (e.g., vibration) indicators.

The partial vacuum can be cycled during at least part of the therapy period to a lower level to vary the force load at the contact surface with the user's skin. Optionally, the controller circuitry is programmable, allowing the user or medical personnel to alter various parameters, such as vacuum levels, alarms, sensor types, etc., as well certain optional features such as noise compensation.

a. Vacuum/Pressure Sensor(s)

As discussed above, a vacuum sensor to determine the differential between the chamber partial vacuum and ambient atmospheric pressure may be connected to the controller, and is used to maintain the partial vacuum at a desired level. Suitable micromachined silicon sensors in pc board-mountable packages are known in the art. These sensors may include temperature compensation or calibration circuitry, or such circuitry may be optionally provided as separate electronic components. A vacuum pressure transducer typically provides a voltage output that is proportional to changing pressure (e.g., increasing vacuum), while an absolute pressure transducer typically provides a voltage output proportional to increasing pressure (e.g., decreasing vacuum).

D. Data Import and Export

The microcontroller is preferably operably connected to a data input device such as a keypad or touchscreen to allow the user or medical personnel to, among other things, set the desired level of partial vacuum. In simple form, a single button may be repeatedly depressed, with the number of button presses counted and converted to a vacuum setting by the microcontroller. In more complicated devices, a display might provide a digital readout of the current setting, and up/down arrow keys used to increase/decrease the setting. Finally, a keypad may be employed to simply type in a desired setting. In all cases, the data input device may communicate with the control module in a wired or wireless manner. In the case where the caregiver is setting the vacuum level, it may be advantageous to have the data input device be either separate or removable from the control module so that alterations cannot be made in an uncontrolled manner.

The apparatuses of the present invention may be configured to record and/or respond to various characteristic sensors. The term "characteristic sensor" as used herein refers to a sensor which detects some characteristic of the user and generates an electronic result corresponding to that characteristic. As noted above, numerous sensor types, such as thermistors, acoustic sensors, oximeters, vibration sensors, etc. are known in the art for sensing respiratory cycles, apnea events, and snoring events. U.S. Patent Publication 2006/0009697, which is hereby incorporated by reference in its entirety, discloses a single, low-profile, disposable system that measures a variety of vital signs, including blood pressure, without using a cuff. This and other information can be easily transferred from a patient to a central monitor through a wired or wireless connection. For example, with the system a medical professional can continuously monitor a patient's blood pressure and other vital signs during their day-to-day activities, or while the patient is admitted to a hospital. This system can also characterize the patient's heart rate and blood oxygen saturation using the same optical system for the blood-pressure measurement. This information can be wirelessly transmitted along with blood-pressure information and used to further diagnose the patient's cardiac condition.

Such sensors may be worn by the user during use of the therapy appliances described herein, and information gathered therefrom transmitted to caregivers or others selected to receive telemetry regarding the appliance. The resulting information has many uses for patients, medical professional, insurance companies, pharmaceutical agencies conducting clinical trials, and organizations for home-health monitoring.

Data import and export may be by wired and/or wireless means. The term "wired" in this context refers to any method in which there is a physical contact which operably connects the control module to an external device, such as a PDA, computer, cellular telephone, network connection, etc., which sends data to or retrieves data from the control module. The term "wireless" refers to any method in which data is sent to or retrieved from the control module without a physical connection.

In the case of a wired data transfer, a cabled USB connection between the control module and the external device is one example that may be provided. While USB type connections have become ubiquitous, any form of connection where contacts on one device physically meet contacts on another device. Alternatively, a memory card, such as a Memory Stick, Secure Digital, Flash memory drive, etc., may be used to transfer data by moving the memory card between the control module and the external device.

In the case of a wireless data transfer, numerous standards well known in the art may be used. Such wireless connections include various radio frequency and optical (e.g., infrared) connections that are known in the art. For relatively short distance RF communications, Bluetooth, HomeRF, IEEE 802.11b, IEEE 802.11a, and IEEE 802.15.4 are well known standard communications protocols that may be used. For somewhat longer range data transfers, cellular telephone protocols such as CDMA, TDMA, GSM, and WAP may be employed.

These methods need not be used in isolation, but instead may be advantageously employed in combination. For example, the control module may communicate at a short distance with a local "base station" by a wired or wireless mechanism, and the base station may then communicate with an external device, for example at a caregiver's office or central data collection point, using one of the cellular telephone protocols, or through telephone twisted pair, cable TV, or other wiring existing in the user's location. This can extend battery life in the control module by lowering power requirements for communication, while the base station may be powered by line voltage.

Numerous battery technologies are known in the art, including common alkaline batteries, oxyride batteries, lithium batteries, etc. There are three preferred battery technologies that could be employed: Nickel Cadmium (NiCad), Nickel Metal Hydride (NiMH) and Lithium Ion (Li-ion), and most preferred are Li-ion batteries. An exemplary power consumption for a battery-powered system will be 45 mA per hour at 4.8 volts. In such a configuration, which can be provided by a 4 cell AAA size NiMH battery pack, the systems described herein could easily operate for an 8-hour sleep period. Alternatively, a 2 cell 300 mAh Li-ion battery pack operating at 7.4 volts can provide similar performance. A most preferred system would operate for an 8-hour period using a single 3.7 volt Li-ion cell providing at least 600 mAh.

In the case of rechargeable batteries, the battery could be provided with a wired plug in to a conventional charger, with contacts which mate with contacts on a battery charging "station," or with an inductive coupling using an inductive coil that would be located on the surface of the vacuum module.

F. Compensating for Movement-Induced Changes Vacuum

Simple body movements can substantially change the force applied to the user's neck, due to movement-induced changes in the internal volume of the appliance. For example, if one considers an appliance having an internal chamber volume of 8.6 cubic inches affixed to an adult male, the act of swallowing can increase the volume of the chamber by some 1.7 cubic inches due to displacement of the throat, a nearly 20% increase.

Although the therapy appliance may have some ability to flex, the appliance must be sufficiently rigid to maintain a spacing between the appliance and the throat. As a result, the movement-induced increase in volume is felt as a sudden increase in the pressure applied to the throat of the user. The air pressure within the therapy appliance may be modeled using the ideal gas law, which provides that the pressure of a gas is related to the volume occupied by that air. The state of an amount of gas is determined by its pressure, volume, and temperature according to the equation $PV=nRT$, where P is the absolute pressure, V is the volume of the vessel, n is the number of moles of gas, R is the universal gas constant, and T is the absolute temperature.

If one assumes that a partial vacuum greater than about 7.6 cm H2O is required to establish a beneficial therapeutic effect, and that movement can suddenly increase the volume enclosed by the therapy appliance by 20% or more due to displacement of the throat, one skilled in the art will recognize that the increase in enclosed volume causes an equivalent 20% increase in the partial vacuum within the therapy appliance. The resulting sudden increase in the forces exerted on the tissues of the throat at the contact surfaces of the appliance can cause discomfort to the wearer, arousal from sleep, etc.

This movement-induced increase in vacuum can be particularly problematic in the case of an integrated ambulatory appliance design, as the vacuum source and associated connections to the vacuum chamber are minimized in volume. As a result, the movement-induced volume changes are more pronounced in percentage terms in comparison to the total vacuum space volume. Said another way, the smaller the volume of the appliance's internal chamber and associated vacuum system, the greater the added force caused by swallowing or coughing.

Thus, a buffering component may be provided to dampen these movement-induced swings in the partial vacuum created within the appliance. This may be modeled most simply as a moveable diaphragm attached to a spring. The spring tension is configured to hold the diaphragm in place when the partial vacuum is within a designed tolerance. That is, if the appliance is designed to produce a partial vacuum of about 18 cm $H_2O$, the spring would not compress or expand at this pressure. The buffer spring may be preloaded at the therapeutic vacuum level by a predetermined amount so that the diaphragm of the appliance is maintained in a predetermined position at that vacuum level. If the desired vacuum level is exceeded, as in the case of the user swallowing, the spring would allow the diaphragm to move to compensate at least in part for the sudden increase in enclosed volume. If the spring is mounted inside the diaphragm (relative to the partial vacuum), the spring would compress; if the spring is mounted outside the diaphragm, the spring would expand. Once the movement had ended, the spring would return to its original shape, thereby returning the diaphragm to its original position. The result is to buffer the increase in pressure felt by the user.

Although described in terms of a spring and diaphragm, other configurations will be readily apparent to those of skill in the art. For example, a buffering component can be provided as a portion of the appliance surface which can flex inward when the internal vacuum exceeds a desired level, and then return to its original position when the vacuum increase subsides.

G. Sound Management and Abatement

As the devices described herein are primarily intended for use during sleep, the ability to minimize disruptions due to noise and/or vibrations can provide clear advantages to the user. Many of the pumping technologies available in the art create substantial noise during use. Moreover, when the pump is cycled on and off during the night, the abrupt changes in sound levels can be particularly disruptive to sleep. In certain embodiments therefore, the devices described herein are coupled with devices that provide improved comfort by managing the sound, masking the sound, and/or cancelling the sound produced during use of the therapeutic appliance.

The term "sound management" as used herein refers to reducing the sound level produced by the device. Motors running at high speed tend to be noisy; low speeds tend to be quiet. As discussed above, DC motor speed is typically controlled by pulse width modulation (PWM). Most positive displacement pumps do not impose a constant torque load on the motor as it rotates 360 degrees. Rather, they have an up stroke and down stroke. When running fast this variation in torque gets lost in the rotor inertia and the motor sounds noisy.

But in a DC motor that is externally commutated, the electronics can determine exactly where in the 360 degree rotation the pump/motor is. In preferred embodiments, the controller is used to increase the electrical pulse width during the rotational portion of the pumping stroke, and decrease the pulse width in the remaining portion of the pumping stroke. By mapping the pump-imposed torque profile of the motor and replicating that with pulse width profile, the pump/motor can be made to run slower, resulting in lower noise and vibration.

In certain embodiments, the therapy appliances of the present invention are combined with sound masking electronics to at least partially mask the noise created by the mechanical and electronic components. The term "sound masking" as used herein refers the addition of natural or artificial sound of a different frequency (more commonly though less-accurately known as "white noise" or "pink noise") into an environment to "mask" or cover-up unwanted sound by using auditory masking. Sound masking reduces or eliminates awareness of pre-existing sounds in a given area and can make a work environment more comfortable, while creating speech privacy so workers can be more productive. Sound masking can also be used in the out-of-doors to restore a more natural ambient environment.

Sound masking is often used in the field of architectural acoustics and in the production of electronic music to mask distracting, undesirable noises. Simple "white noise" machines can be very simple, involving an enclosed fan and (optionally) a speed switch. This fan drives air through small slots in the machine's casing, producing the desired sound. More complex machines may be electronic, and offer a variety of "nature sounds." A Sound generator may be carried on the appliance itself, as depicted in FIG. 9, or may be provided as a separate unit.

Similarly, in certain embodiments, the therapy appliances of the present invention are combined with sound cancelling electronics to at least partially mask the noise created by the mechanical and electronic components. The term "sound cancellation" as used herein refers to the provision of phase cancellation pressure waves. Sound may be considered a pressure wave, which consists of a compression phase and a rarefaction phase. A noise-cancellation speaker emits a sound wave with the same amplitude and the opposite polarity (in antiphase) to the original sound. The waves combine to form a new wave, in a process called interference, and effectively cancel each other out—an effect which is called phase cancellation. Depending on the circumstances and the method used, the resulting sound wave may be so faint as to be inaudible to human ears.

Cyclic sounds, even complex ones, are easier to cancel than random sounds due to the repetition in the wave form. Thus, sound cancellation is particularly applicable to the present invention. In preferred embodiments, a microphone is placed near the ear, and electronic circuitry which generates an "antinoise" sound wave with the opposite polarity of the sound wave arriving at the microphone is delivered through speakers placed at the ear in the form of headphones or earbuds. This results in destructive interference, which cancels out the noise within the enclosed volume of the ear. Noise cancellation circuitry or sound masking circuitry may be carried on the appliance itself, or may be provided as a separate unit. Sound from the circuitry can be provided through small speakers or earbuds.

H. Additional Elements

WO08/076,421 and WO09/143,259, each of which is hereby incorporated by reference in its entirety including all tables, figures and claims, describe negative pressure therapy appliances for relieving airway obstruction. These publications describe various elements which may be provided in various combinations with the apparatus of the present invention. These elements include the following.

A first combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$; and an air pump operably connected to the chamber and configured to maintain a partial vacuum within said chamber at a level between 7.6 cm and 61 cm of water while generating a sound level of less than 40 dB SPL.

A second combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$; and an air pump operably connected to the chamber and configured to maintain a partial vacuum within said chamber, wherein said air pump comprises a positive displacement pump.

A third combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$, wherein said therapy appliance comprises a buffering component configured to dampen swings in the partial vacuum created within the appliance by user movement; and an air pump operatively connected to the space-filled chamber to provide a partial vacuum within the chamber.

A fourth combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$, wherein said peripheral edge is configured to provide a pressure along the contact surface with the user's skin of 60 mm Hg or less at a partial vacuum level within said enclosed volume of between about 7.6 cm to about 61 cm of water; and an air pump operably connected to the chamber and configured to maintain a partial vacuum within said chamber A fifth combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$ and having a vacuum control module comprising a microcontroller coupled to a vacuum or pressure sensor and motor control circuitry which controls the pump on/off cycles and/or speed.

A sixth combination provides a therapy appliance which is a biocompatible single integral element that provides a seal at the skin interface having a low leakage rate of air into the enclosed chamber, preferably a rate of between 0.005 and 0.5 in$^3$/min, and most preferably at 0.01 and 0.1 in$^3$/min; a diaphragm pump having a single stroke displacement of between 0.001 and 0.01 in$^3$, and most preferably in the range of 0.003 to 0.005 in$^3$, driven using a rotary brushless DC motor or a linear DC motor; and a vacuum control module comprising a microcontroller coupled to a vacuum or pressure sensor and motor control circuitry which controls the pump on/off cycles and/or speed.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. An apparatus configured to seat against the chin and neck of a patient to define a space-filled chamber at an external location approximately at the soft tissue of the patient associated with the anterior triangle of the neck, the apparatus adapted to maintain patency of the upper airway by applying a force to a surface of the neck of the patient to draw the surface into the space-filled chamber when a therapeutic level of negative pressure is applied within the space-filled chamber, comprising:

a dome having a peripheral edge;

a flange extending around the peripheral edge of the dome, wherein the flange is adapted to contact a region of the patient's neck lying between the thyroid cartilage and the jugular notch, wherein a portion of the flange is adapted to extend over the patient's mental protuberance; and a shelf adapted to rest under the patient's chin;

wherein the shelf extends from the peripheral edge of the dome opposite to the portion of the flange extending over the patient's mental protuberance and terminates prior to the patient's angle of mandible;

wherein the shelf in combination with the peripheral edge of the dome and the portion of the flange extending over the patient's mental protuberance forms a chin cup adapted to receive the patient's chin and to ensure proper placement of the apparatus onto the patient's chin; and wherein at least a portion of the flange comprises a concave profile in the absence of a force load that is applied onto the flange when the therapeutic level of negative pressure is applied within the space-filled chamber, and wherein the concave profile is adapted to be flattened on the patient's skin when the force load is applied when the therapeutic level of negative pressure is applied within the space-filled chamber.

2. The apparatus of claim 1, wherein the flange is adapted to contact a region of the patient's neck proximate to the cricoid cartilage.

3. The apparatus of claim 1, wherein the flange is attached to the peripheral edge by a pivoting member, said pivoting member adapted to provide movement of the flange relative to the peripheral edge in order to allow the flange to adjust the skin contact surface of the flange to the contour of the patient's neck.

4. The apparatus of claim 3, wherein the flange, peripheral edge, and pivoting member are formed in an integral fashion.

5. The apparatus of claim 3, wherein the flange, peripheral edge, and pivoting member are formed in a non-integral fashion such that the flange is a replaceable component of the apparatus.

6. The apparatus of claim 1, wherein the flange comprises flexural elements located within the flange configured to reduce longitudinal stress within the flange.

7. The apparatus of claim 1, wherein the flange comprises a breathable material inherent in, or positioned on, all or a portion of the skin contact surface of the flange, wherein the breathable material is configured to provide a controlled flow of air through the breathable material and into the space-filled chamber when the therapeutic level of negative pressure is applied within the space-filled chamber.

8. The apparatus of claim 7, wherein the breathable material provides a controlled air flow rate greater than about 0.1 standard cubic feet per minute.

9. The apparatus of claim 7, wherein the breathable material is a disposable material positioned on all or a portion of the skin contact surface of the flange.

10. The apparatus of claim 7, wherein the breathable material is held to the flange by an adhesive layer provided on a surface of the breathable material.

11. The apparatus of claim 7, wherein the breathable material is a component of a lamination stack.

12. The apparatus of claim 7, wherein the breathable material is an inherent structural feature in all or a portion of the skin contact surface of the flange.

13. The apparatus of claim 12, wherein the breathable material is a textured surface of the flange.

14. The apparatus of claim 13, wherein the textured surface comprises features having a depth from about 0.0005 inches to about 0.020 inches.

15. The apparatus of claim 1, wherein the flange comprises a tacky material inherent in, or positioned on, all or a portion of the skin contact surface of the flange.

16. The apparatus of claim 15, wherein the tacky material comprises a room-temperature vulcanizing (RTV) silicone.

17. The apparatus of claim 1, wherein the flange is radiused at an edge thereof over at least a portion of the flange.

18. The apparatus of claim 1, wherein the flange varies in thickness, with a minimum thickness at an edge of the flange, and wherein the edge of the flange flexes under load to provide a radiused edge.

19. The apparatus of claim 18, wherein the flange thickness varies from a maximum thickness of between 0.4 inches to 0.1 inches, and a minimum thickness of 0.02 inches or less.

20. The apparatus of claim 19, wherein the maximum thickness is between 0.312 inches and 0.25 inches, and the minimum thickness is between 0.01 and 0.005 inches.

21. The apparatus of claim 1, wherein the flange varies in thickness from a maximum thickness of between 0.4 inches to 0.1 inches, and a minimum thickness of 0.02 inches or less.

22. The apparatus of claim 21, wherein the maximum thickness is between 0.312 inches and 0.25 inches, and the minimum thickness is between 0.01 and 0.005 inches.

23. The apparatus of claim 1, further comprising a low friction material having a coefficient of friction of about 0.65 or less on all or a portion of the skin contact surface of the flange, wherein the low friction material is configured to provide local movement of the flange relative to the skin surface.

24. The apparatus of claim 23, wherein a portion of the peripheral edge which is proximate to the patient's chin does not comprise the low friction material.

25. The apparatus of claim 23, wherein the low friction material has a coefficient of friction of less than about 0.5.

26. The apparatus of claim 1, wherein the apparatus is configured to produce negative pressure by manual compression of the space-filled chamber while the apparatus is seated against the patient, followed by allowing the space-filled chamber to return to an uncompressed state.

27. The apparatus of claim 1, further comprising an air pump operably connected to the apparatus to produce negative pressure within the space-filled chamber.

28. The apparatus of claim 27, wherein the air pump is a manual squeeze bulb.

29. The apparatus of claim 27, wherein the air pump is configured to be wearable by the patient and is battery powered.

30. The apparatus of claim 27, wherein the air pump is configured integrally to the apparatus.

31. The apparatus of claim 27, wherein the air pump comprises a piezoelectric material configured to provide an oscillatory pumping motion.

32. The apparatus of claim 31, wherein the oscillatory pumping motion operates at a frequency greater than 500 Hz.

33. The apparatus of claim 27, wherein the air pump is a component of an air handling system which controls temperature, humidity, and air flow within the space-filled chamber.

34. The apparatus of claim 27, wherein the air pump is connected to the apparatus via a hose or tube.

35. The apparatus of claim 1, further comprising an integral sealing member external to the flange which forms an enclosed air channel around all or a portion of the apparatus edge.

36. The apparatus of claim 1, further comprising an integral sealing member underlying all or a portion of a skin contact surface of the flange, wherein an interface between the integral sealing member and the flange provides a low friction region configured to provide local movement of the of the flange relative to the skin contact surface.

37. The apparatus of claim 36, wherein a lubricating fluid is placed between the integral sealing member and the flange to reduce friction at the interface.

38. The apparatus of claim 1, further comprising a fabric apparatus which is configured to fasten around the patient's neck to secure the apparatus to the patient.

39. An apparatus configured to seat against the chin and neck of a patient to define a space-filled chamber between an inner surface of the apparatus and the skin of the patient at an external location approximately at the soft tissue of the patient associated with the anterior triangle of the neck, the apparatus adapted to maintain or increase patency of the upper airway by applying a vacuum-derived force to a surface of the neck of the patient when a therapeutic level of negative pressure is applied within the space-filled chamber, wherein the apparatus is sufficiently rigid to withstand the therapeutic level of negative pressure within the space-filled chamber, the apparatus comprising:
- a dome having a peripheral edge adapted to contact the skin of the patient in order to enclose the space-filled chamber; and
- a flange extending around the peripheral edge of the dome, wherein the flange is adapted to contact a region of the patient's neck lying between the thyroid cartilage and the jugular notch, wherein a portion of the flange is adapted to extend over the patient's mental protuberance; and
- a shelf adapted to rest under the patient's chin;
- wherein the shelf extends from the peripheral edge of the dome opposite to the portion of the flange extending over the patient's mental protuberance and terminates prior to the patient's angle of mandible, wherein the shelf in combination with the peripheral edge of the dome and the portion of the flange extending over the patient's mental protuberance forms a chin cup adapted to receive the patient's chin and to ensure proper placement of the apparatus onto the patient's chin.

40. An apparatus according to claim 39, wherein all or a portion of the peripheral edge comprises a fluid-filled enclosure.

41. An apparatus according to claim 40, wherein the fluid-filled enclosure comprises a fluid, gel, or foam material.

* * * * *